United States Patent
Richter et al.

(10) Patent No.: US 10,390,745 B2
(45) Date of Patent: Aug. 27, 2019

(54) ELICITING A BLOOD SAMPLE

(71) Applicant: Sanofi-Aventis Deutschland GmbH, Frankfurt am Main (DE)

(72) Inventors: Frank Richter, Bad Tolz (DE); Ross Macarthur, Cheshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 152 days.

(21) Appl. No.: 14/345,600

(22) PCT Filed: Sep. 21, 2012

(86) PCT No.: PCT/EP2012/068699
§ 371 (c)(1),
(2) Date: Mar. 18, 2014

(87) PCT Pub. No.: WO2013/041705
PCT Pub. Date: Mar. 28, 2013

(65) Prior Publication Data
US 2014/0378800 A1    Dec. 25, 2014

(30) Foreign Application Priority Data
Sep. 22, 2011    (EP) ..................................... 11182383

(51) Int. Cl.
*A61B 5/151*    (2006.01)
*A61B 5/15*    (2006.01)
(Continued)

(52) U.S. Cl.
CPC ........ *A61B 5/15174* (2013.01); *A61B 5/1411* (2013.01); *A61B 5/14532* (2013.01);
(Continued)

(58) Field of Classification Search
CPC ............ A61B 5/15174; A61B 5/14532; A61B 5/15113; A61B 5/150526;
(Continued)

(56) References Cited

U.S. PATENT DOCUMENTS 1,579,679 A * 4/1926 Wahrt ..................... A61H 7/001
601/97
4,794,926 A * 1/1989 Munsch ............... A61B 5/1411
606/183
(Continued)

FOREIGN PATENT DOCUMENTS

JP    H09-84781 A    3/1997
JP    2002-065648 A    3/2002
(Continued)

OTHER PUBLICATIONS

English Translation of the Abstract of Japanese Patent Application No. H09-84781 dated Oct. 26, 2017.
(Continued)

*Primary Examiner* — David J. McCrosky
(74) *Attorney, Agent, or Firm* — McCarter & English, LLP (57) ABSTRACT

Within examples, an apparatus for eliciting a blood sample includes a testing member rotatably mounted on a shaft; and an aperture for positioning a body part of the user relative to the edge of the testing member, wherein an edge of the testing member is shaped such as repeatedly to exert pressure on the skin of a user when the testing member is rotated.

14 Claims, 9 Drawing Sheets

(51) Int. Cl.
*A61B 5/157* (2006.01)
*A61B 5/145* (2006.01)
*G01N 33/487* (2006.01)

(52) U.S. Cl.
CPC ........ *A61B 5/157* (2013.01); *A61B 5/150022* (2013.01); *A61B 5/150068* (2013.01); *A61B 5/15113* (2013.01); *A61B 5/15153* (2013.01); *A61B 5/150175* (2013.01); *A61B 5/150427* (2013.01); *A61B 5/150519* (2013.01); *A61B 5/150526* (2013.01); *A61B 5/15126* (2013.01); *G01N 33/48757* (2013.01)

(58) Field of Classification Search
CPC ............ A61B 5/150175; A61B 5/1411; A61B 5/150068; A61B 5/150427; A61B 5/157; A61B 5/150022; A61B 5/15153; A61B 5/150519; A61B 5/15126
See application file for complete search history.

(56) References Cited

U.S. PATENT DOCUMENTS

| | | | |
|---|---|---|---|
| 7,201,723 B2 * | 4/2007 | Chan | A61B 5/1411 600/573 |
| 8,333,715 B1 * | 12/2012 | Alferness | A61B 5/1411 600/575 |
| 8,870,903 B2 | 10/2014 | LeVaughn et al. | |
| 9,332,931 B2 | 5/2016 | Chan | |
| 2004/0098009 A1 * | 5/2004 | Boecker | A61B 5/1411 606/181 |
| 2007/0112367 A1 | 5/2007 | Olson | |

FOREIGN PATENT DOCUMENTS

| | | |
|---|---|---|
| JP | 2004-12886 A | 1/2004 |
| JP | 2006512932 A | 4/2006 |
| JP | 2007136198 A | 6/2007 |
| JP | 2007530162 A | 11/2007 |
| WO | 2005018709 A2 | 3/2005 |
| WO | 2005118690 A1 | 12/2005 |
| WO | 2009037192 A1 | 3/2009 |
| WO | 2010056869 A2 | 5/2010 |

OTHER PUBLICATIONS

English Translation of the Abstract of Japanese Patent Application No. 2002-065648 dated Oct. 26, 2017.

English Translation of the Abstract of Japanese Patent Application No. 2004-012886 dated Oct. 26, 2017.

* cited by examiner

ELICITING A BLOOD SAMPLE

CROSS REFERENCE TO RELATED APPLICATIONS

The present application is a U.S. National Phase Application pursuant to 35 U.S.C. § 371 of International Application No. PCT/EP2012/068699 filed Sep. 21, 2012, which claims priority to European Patent Application No. 11182383.7 filed Sep. 22, 2011. The entire disclosure contents of these applications are herewith incorporated by reference into the present application.

FIELD OF INVENTION

This invention relates to method and apparatus for eliciting a blood sample.

BACKGROUND

Diabetes sufferers may be provided with quantities of insulin, for instance by injection, sometimes a number of times daily. The quantity of insulin that is appropriate depends on the person's blood glucose level, so blood glucose level measurement can also occur a number of times daily.

Blood glucose level measurement typically is a multi stage process. The first is lancing, in which a lancet, or needle, is used to pierce the skin of a user, for example on the end or side of a finger. Once a suitable amount of blood has been produced, a sample is taken on a testing strip. A person may need to squeeze their finger in order to cause sufficient blood to be expelled. Sometimes lancing needs to be reperformed. The testing strip then is provided to a meter, typically an electronic meter, which analyses the sample, for example by determining a parameter (e.g. an electrochemical potential or voltage, resulting from a chemical reaction between the blood sample and an enzyme present in the testing strip, and provides a blood glucose measurement result. This measurement is then used to determine an amount of insulin to be consumed by the person.

SUMMARY

A first aspect of the invention provides apparatus for eliciting a blood sample, the apparatus comprising;
  a testing member rotatably mounted on a shaft; and
  an aperture for positioning a body part of the user relative to the edge of the testing member,
    wherein an edge of the testing member is shaped such as repeatedly to exert pressure on the skin of a user when the testing member is rotated.

The aperture for positioning the body part may be part of a housing having, the shaft being mounted inside the housing.

The apparatus may further comprise a lancet protruding from one position at an edge of the testing member, the lancet being configured to piece the skin of the user's body part when in a first rotational position.

The edge of the testing member may be shaped as a plurality of ridges. The edge of the testing member may be shaped as three ridges. The ridges may be curved, optionally sinusoidal.

First ends of one or more capillaries may be disposed on each of the plurality of ridges on an edge of the testing member. A first end of a capillary may be disposed approximately at the crest of each ridge on an edge of the testing member. Each of the one or more capillaries may extend through the body of the testing member and may terminate at a blood collection part supported on or within the testing member.

The testing member may further comprise at least two electrical contact points connected to the blood collection part for communication with a meter for determining a parameter of blood chemistry.

The blood collection part may comprise an absorbent material which contains an enzyme for blood glucose determination. The blood collection part may have a higher capillary pull force than the capillaries.

The apparatus may be configured to control the speed of rotation of the testing member such that, having regard to the spacing between adjacent ridges, the frequency of the periodic pressure applied to a user's body part is consistent with the common thickness and elasticity of human skin.

The frequency may encourage venous blood to exit a puncture wound in the user's body part or alternatively the frequency may encourage plasma blood to exit a puncture wound in the user's body part.

A second aspect of the invention provides a method for eliciting a blood sample, the method comprising;
  providing a testing member rotatably mounted on a shaft and an aperture for positioning a body part of a user relative to an edge of the testing member; and
  rotating the testing member so that an edge of the testing member exerts periodic pressure on the skin of the user.

BRIEF DESCRIPTION OF THE DRAWINGS

Embodiments of the invention will now be described, by way of example only, with reference to the accompanying drawings, in which.

DETAILED DESCRIPTION

Figure 1:
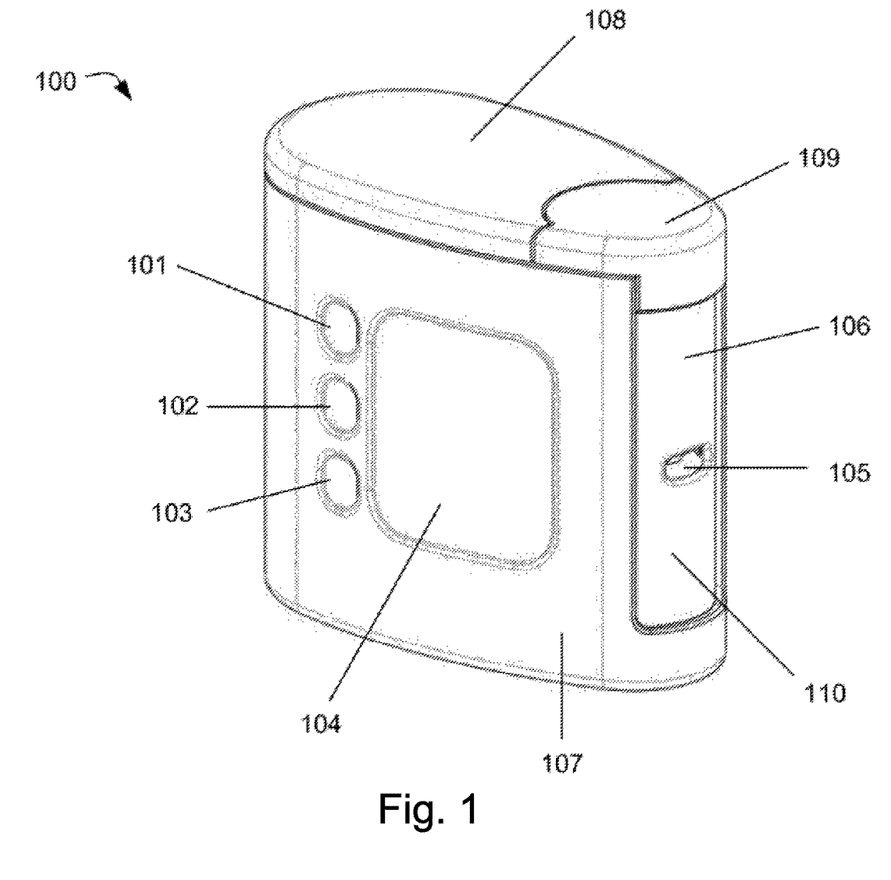
FIG. 1 is a perspective view of a blood glucose meter (BGM) according to aspects of the invention.

A blood glucose meter (BGM) 100 is shown in FIG. 1. The BGM 100 is shown in a perspective view. The BGM 100 has a generally flat base, that is not visible in the figure. The BGM 100 is approximately as tall as it is long, and its width is approximately one-third of its height.

On one side face of the BGM are provided first, second and third inputs 101, 102, 103. These may take the form of push-switches or touch sensitive transducers, for instance.

Also provided on the side of the BGM next to the input devices 101 to 103 is a display 104. This may take any suitable form, for instance a liquid crystal display (LCD), e-ink etc. In use, a user may control the BGM 100 using the input devices 101 to 103 and may be provided with information by the BGM through the display 104.

Located at a front face of the BGM 100 is an aperture 105. The aperture 105 is located at approximately half of the height of the BGM. The aperture 105 is configured such as to be able to receive a part of a user's body, for the purpose of extracting a blood sample therefrom. For instance, the aperture 105 may be dimensioned so as to receive an end or a side part of a finger or thumb, or may be dimensioned so as to receive a side of a user's hand or a pinch of skin from a user's arm. The aperture may be rectangular in shape. Its edges may be bevelled, so as to guide a user's digit into a specific location.

The aperture 105 is provided in the side of a cartridge 106. The cartridge 106 has a generally cylindrical form, and is arranged vertically in the BGM 100.

In particular, the BGM includes a first housing part 107. The first housing part 107 forms the base, left and right side face and the rear face of the BGM 100. On the front face of the BGM 100, the first housing part 107 also comprises the lowermost part of the side face. A fixed lid part 108 is attached to the first housing part 107. The fixed lid part 108 comprises most of the top surface of the BGM 100. A removable lid part 109 comprises the remaining part of the top surface of the BGM 100. The removable lid part is disposed above the cartridge 106 at the front face of the BGM 100. The first housing part 107, the fixed lid part 108 and the removable lid part 109 are configured such that when the removable lid part is in place on the BGM the cartridge 106 is retained by mechanical interaction between the three components but is removable by a user. The exact way in which the removable lid part 109 is released from the BGM 100 is not critical and is not described in detail here.

The first housing part 107 is configured such as to provide an elongate aperture 110 at the front face of the BGM 100. The elongate aperture 110 may extend for most of the height of the front face of the BGM 100. The elongate aperture 110 is defined at the uppermost part by the removable lid part 109 and is defined by the first housing part 107 at the right, left and bottom. The BGM 100 is arranged such that the cartridge 106 occupies the whole of the area of the elongate aperture 110. The diameter of the cartridge 106 is greater than the width of the aperture 110 by a factor for instance of between 5 and 50%. The cartridge 106 has a length that is between 3 or 4 times its diameter.

A slidable or pivotable door in the housing part 107 of the BGM 100 may cover all or a part of the elongate aperture 110 when the BGM is not in use. The door may cover at least the aperture 105, such as to prevent the ingress of dirt and other potential contaminants into the aperture 105.

The removable lid part 109 is configured such that when removed from the BGM 100 the cartridge 106 is able to be extracted from the BGM by moving it vertically along its axis. When the cartridge 106 is fully removed, the elongate aperture 110 reveals a cavity in the BGM 100. A replacement cartridge can then be introduced into the BGM 100 in the opposite manner to which the old cartridge 106 was removed. The cartridge 106 and the cavity which receives the cartridge may have a keying feature, such as a protrusion and a groove, a non circular diameter, or the like. Thus, when the cartridge 106 is fully inserted, the aperture 105 is in a fixed position to the elongate aperture 110, for example in a centred position.

Figure 2A:
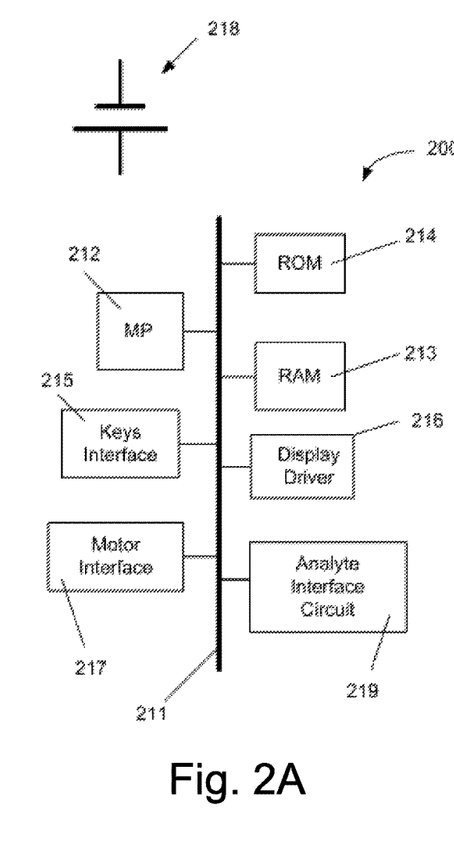
FIG. 2A illustrates components of one embodiment the BGM of FIG. 1 including electronic components.
Figure 2B:
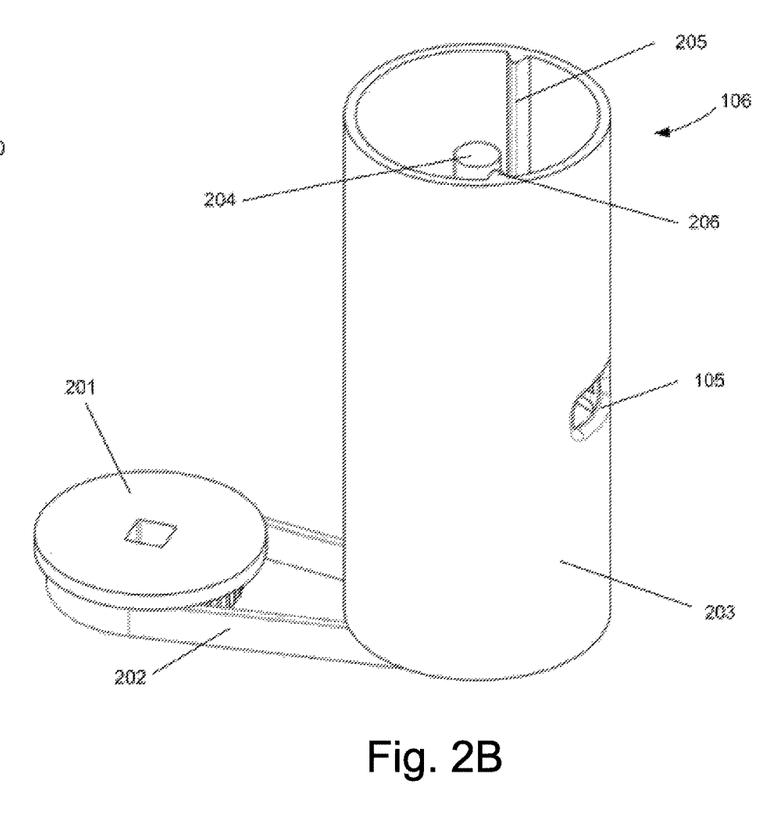
FIG. 2B illustrates components of one embodiment the BGM of FIG. 1 including a cartridge.

FIG. 2B shows a subsystem 200 of the blood glucose meter 100. The subsystem 200 includes the cartridge 106, a drive wheel 201 and a drive belt 202.

In FIG. 2B, the cartridge shown as having a hollow cylindrical housing part 203, which constitutes part of a housing. The aperture 105 is formed in the hollow cylindrical housing part 203. Coaxial with the hollow cylindrical part 203 is an elongate shaft 204, only the top part of which is illustrated in FIG. 2B. The length of the shaft 204 is such that its uppermost end is slightly below the uppermost end of the hollow cylindrical housing part 203. As will be described below, the shaft 204 is mechanically coupled with the drive belt 202 so as to be rotatable by rotation of the drive wheel 201.

Formed with the inner surface of the hollow cylindrical housing part 203 are first and second guide members 205, 206. In FIG. 2B, it can be seen that the first and second guide members 205, 206 have a generally triangular cross section. One side of the triangular cross section of the first and second guide members 205, 206 is integral with the inner surface of the hollow cylindrical housing part 203, with a point of the triangular cross section extending towards the centre of the cartridge 106. A part of the length of the first guide member 205 is visible in FIG. 2B, but only the uppermost surface of the second guide member 206 is visible in that figure.

FIG. 2A also shows some electronic components that form parts of the blood glucose meter 100. These components are provided within the housing 107 but do not form part of the cartridge 106.

A bus 211 is arranged to connect a number of components including a microprocessor 212, random access memory (RAM) 213, read-only memory (ROM) 214, a keys interface 215, a display driver 216, an analyte interface circuit 219 and a motor interface 217. All of these components are powered by a battery 218, which may take any suitable form.

Stored in the ROM 214 is software and firmware that governs operation of the blood glucose meter 100. The software/firmware is executed by the microprocessor 212 using the RAM 213. The software/firmware stored in the ROM 214 is operable to operate the blood glucose meter 100 such as to allow control by a user through the keys or input devices 101 to 103, as detected by the keys interface 215. A blood glucose measurement and other information is provided on the display 104 at suitable times by operation of the software/firmware and the microprocessor 212 through the display driver 216.

The motor interface 217 allows the microprocessor 212, according to the software/firmware stored in the ROM 214, to control the motor that is coupled to the drive wheel 201, and any other motors that are included in the blood glucose meter 100 (as will be described below).

The analyte interface circuit 219 is operable to provide electrical signals with certain voltages to the electrical contact terminals 401 (described in more detail with respect to FIG. 8), and thus the contact pads 318 and thus the blood collection part 315 (described in more detail with respect to FIG. 3), and to measure parameters of signals such as to allow the microprocessor 212 to measure a blood glucose level of a blood sample.

Figure 3:
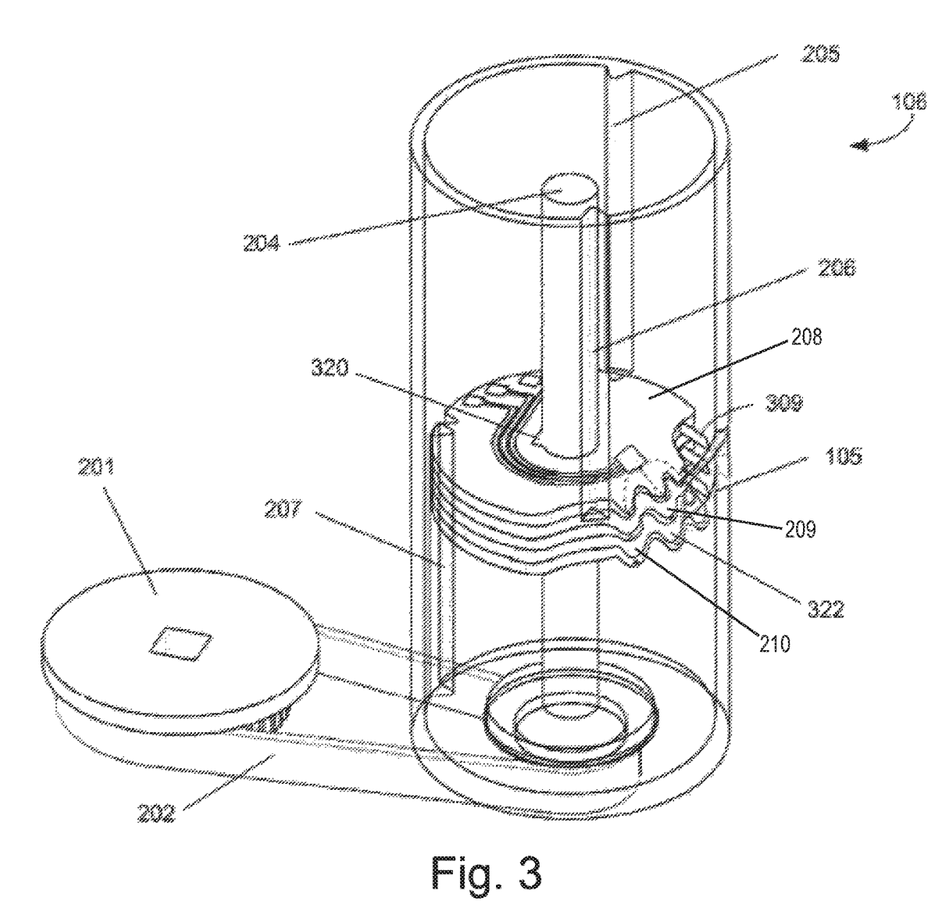
FIG. 3 is a perspective view of components of the BGM of FIG. 2 but with a hollow cylindrical housing part shown as transparent.

FIG. 3 is the same as FIG. 2B except that the hollow cylindrical housing part 203 is shown in wire frame, so as to reveal components internal to it, and in that the electronic components are omitted. In FIG. 3, a third guide member 207 is visible. As can be seen from this figure, the first and second guide members 205, 206 are located only in the uppermost half of the length of the cartridge 106, and the third guide member 207 is located only in the lowermost half of the cartridge 106. The first, second and third guide members 205 to 207 are distributed around the circumference of the hollow cylindrical housing part 203. In particular, the first and second guide members 205, 206 are located at approximately 100 to 160 degrees from one another. The third guide member 207 is located approximately 60 to 130 degrees from each of the first and second guide members 205, 206.

Mounted on the shaft 204 are a plurality of members, three of which are shown in FIG. 3 as 208, 209 and 210 respectively. The members 208 to 210 will hereafter be referred to as test disc members. Each of the test disc members 208 to 210 is substantially the same.

Figure 4:
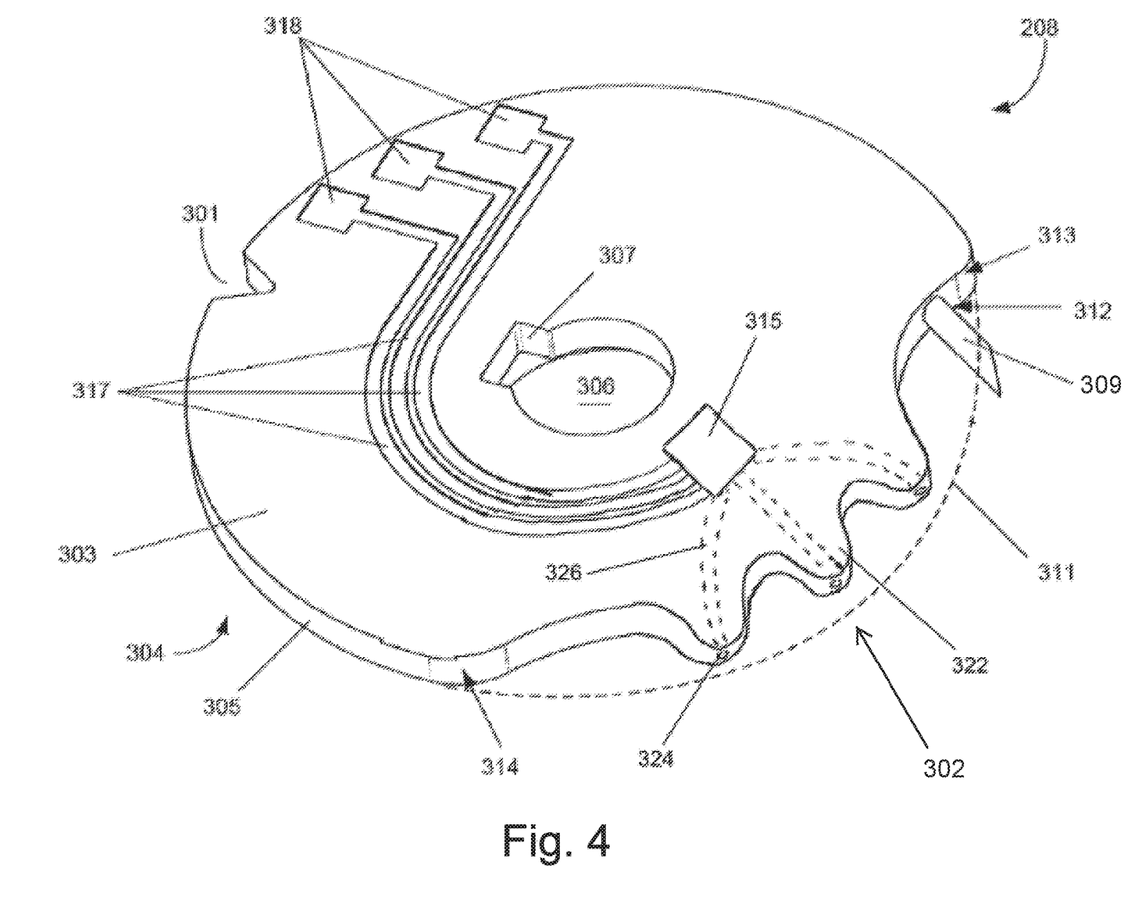
FIG. 4 is a perspective view of a test disc member forming part of the BGM of FIGS. 1 and 2.

One test disc member 208 is shown in some detail in FIG. 4. The test disc member 208 has a generally circular shape, although on one side a notch 301 is formed and on another side a cutaway portion 302 is provided. The cutaway portion 302 comprises a number of ridges or protrusions 322 and constitutes a milking portion.

Figure 5:
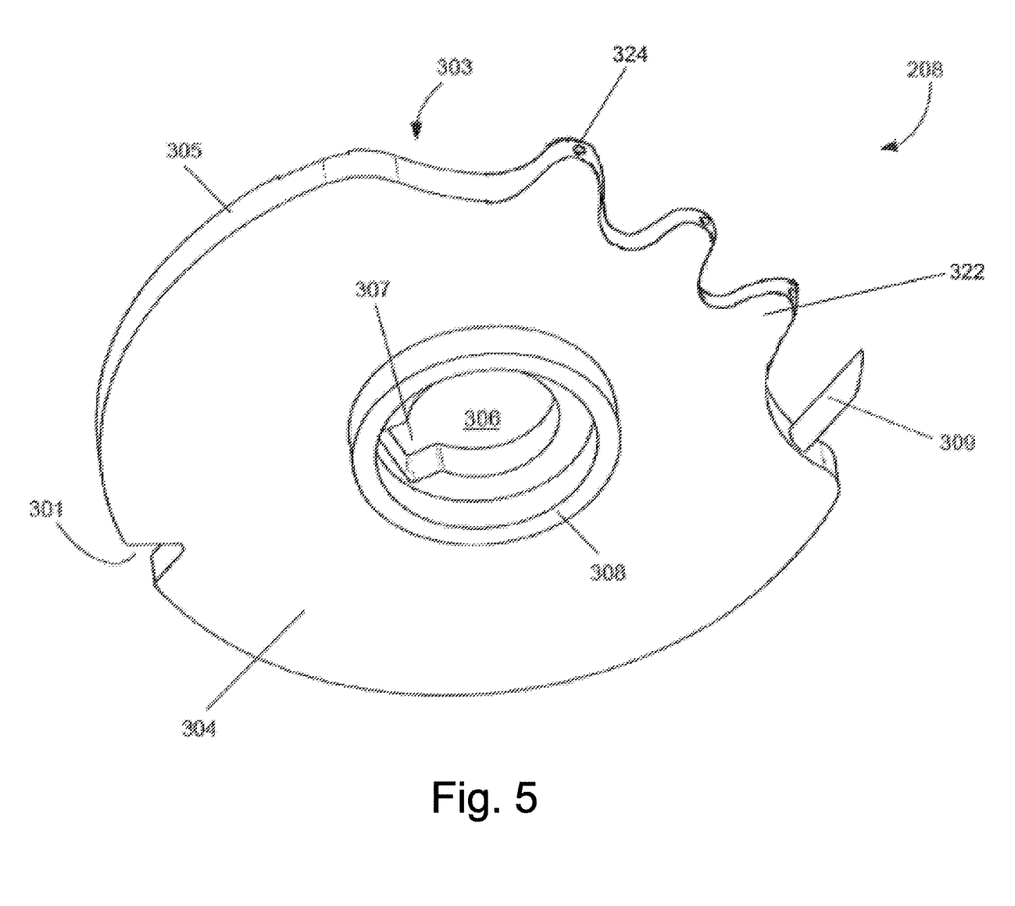
FIG. 5 is an underneath perspective view of the test disc member of FIG. 4.

The test disc member 208 includes an uppermost surface 303, a lowermost surface 304, which is shown in FIG. 5, and a disc edge 305. The diameter of the test disc member 208 is between 15 and 25 millimeters, for instance 20 millimeters. The thickness of the disc, which is equal to the height of the disc edge 305, is between 0.5 millimeters and 1 millimeter. FIG. 5 shows the test disc member 208 from the underside. As such, the lower surface 304 is visible and the upper surface 303 is not visible. The test disc member 208 will now be described with reference to FIGS. 4 and 5.

A hole 306 is formed at the centre of the test disc member 208. The hole 306 comprises two main parts. A circular part is centred on the test disc member 208 and has a diameter equal to or slightly larger than the external diameter of the shaft 204. A drive notch 307 abuts the circular part of the hole 306 and includes edges that are able to be engaged by a drive dog.

A drive dog 320 is formed on the shaft 204. The drive dog 320 is engaged with the drive notch 307 in the hole 306 of the test disc member 208. This engagement allows rotation of the shaft 204 to result in rotation of the test disc member 208.

On the underside of the test disc member 208 is provided a spacer member 308. The spacer member 308 comprises a slice of a hollow cylinder. The cylinder is centred on the centre of the test disc member 208. The inner diameter of the spacer member 308 is selected such that the hole 306 does not overlap with the spacer member 308. The outer diameter of the spacer member 308 is only slightly greater than the inner diameter, so the spacer member 308 has little thickness. The height of the spacer member 308 is between 0.5 and 1 millimeter. When plural test disc members are stacked together, the spacer member 308 provides separation between the upper surface 303 of one test disc member and the lower surface 304 of the test disc member that is directly above it. The separation is determined by the height of the spacer member 308.

Referring again to FIG. 4, a lancet 309 is shown protruding from the disc edge 305. The lancet 309 is provided in the cutaway portion 302. A first end of the lancet 309 is embedded within the material of the test disc member 208, and a second end is provided with a sharp point and extends outwardly. The lancet 309 extends at an angle between 30 and 60 degrees from a radius line of the test disc member 208 at the position where the end of the lancet 309 is embedded in the test disc member. The second end of the lancet 309 is located at or just outside a circumference 311 of the test disc member 208. The circumference 311 is shown as a dotted line in FIG. 4 because it is virtual, instead of tangible. The lancet 309 extends from the disc edge 305 at a first position 312 on the disc edge. The first position 312 is close to a second position 313 at which the cutaway portion 302 starts. The cutaway portion 302 ends at a third position 314. Between the second and third positions 313, 314 opposite to the cutaway portion 302, the disc edge 305 generally takes the form of a circle, although the notch 301 interrupts that circle.

The cutaway portion 302 comprises a number of ridges 322. The ridges 322 may have a partly or completely curved profile. For instance, they may be sinusoidal in shape.

FIGS. 4 and 5 show a test disc member 208 having three ridges 322, however the test disc may have any number of ridges greater than two, for example between two and twelve ridges. The ridges 322 do not extend beyond the boundary of the test disc circumference 311.

Some or all of the ridges 322 may have one or more capillary openings 324. The capillary openings 324 are provided in the edge 305 of the test disc member 208. The capillary openings 324 may be provides at the crests of the ridges 322, i.e. the parts at the maximum distance from the centre of the disc 208.

Alternatively, an area of the test disc edge 305 at and around the crest of each ridge may be composed of an absorbent material. In these embodiments, capillaries 326 extend through the body of the test disc member 208 away from the capillary openings 324.

A blood collection part 315 is located within the body of the test disc member 208. A recess may be provided in the upper surface 303 of the test disc member 208 to receive the blood collection part 315. Each of the capillaries 326 terminates at the blood collection part 315. The blood collection part may be formed of an absorbent material containing an enzyme for blood glucose determination, or some other parameter measurement. Blood may be drawn into the blood collection part 315 through capillary action. The material of the blood collection part 315 may have a higher capillary "pull-force" than the capillaries 326, such that the blood collects in the blood collection part 315 rather than in the capillaries 326.

The enzyme in the blood collection part 315 reacts chemically with blood in such a way that blood glucose level can be measured. The blood collection part 315 is connected to first to third contact pads 318 by first to third conductive tracks 317. The contact pads 318 and the conductive tracks 317 are formed on the upper surface 303 of the test disc member 208.

The aperture 105 is configured such as to allow an amount of the flesh making up the end of the user's digit to be present within the internal volume of the cylindrical part 203 when the user presses the digit up against the aperture 105. When the user applies force into the aperture 105 with the digit, the digit distorts and a bulbous part is provided within the internal diameter of the hollow cylindrical housing part 203. The size of the bulbous part, and in particular the height of the bulbous part, depends on a number of factors, including the physical characteristics of the user's digit and the amount of force that the user applies, as well as the configuration of the aperture 105. The aperture 105 is dimensioned such that in normal use (i.e. with a typical user applying a typical amount of force) a bulbous part of the user's digit extends into the internal volume of the hollow cylindrical housing part 203 to a depth of approximately 1 millimeter.

In use a part of a user is firstly pierced by the lancet 309, the part is then milked by the ridges 322, and blood then is provided to the blood collection part 315 through the capillaries 326. A measuring circuit connected to the blood collection part 315 by way of the conductive tracks 317 and the contact pads 318 then is able to determine a blood glucose level of the user. The level then is displayed on the display 104.

Operation will now be described with reference to the figures.

As shown in FIG. 3, the test disc members 208 to 210 commence at the same orientation. Here, the first test disc member 208 is uppermost. The third guide member 207 is located in the notch 301 of the lowermost test disc members 209, 210. The notch 301 of the first test disc member 208 is aligned with the third guide member 207, but is not constrained thereby. The upper surface 303 of the uppermost test disc member 208 is in contact with a lowermost surface of the first guide member 205. The lowermost surface of the second guide member 206 is at the same level as the lowermost end of the first guide member 205. However, the second guide member 206 coincides with part of the cutaway portion 302 of the first test disc member 208 at the orientation of the test disc member 208 shown in FIG. 3. As such, there is no contact between the second guide member 206 and the first test disc member 208 when the first test disc member is in this position. The test disc members 208 to 210 are biased in an upwards direction by bias means (not shown), which may be a spring. However, the test disc members 200 to 210 are prevented from moving upwards within the cartridge 106 by virtue of the contact between the upper surface 303 of the first test member 208 and the lowermost end of the first guide member 205.

At the position shown in FIG. 3, the distal end of the lancet 309 is not co-located with the aperture 105. As such, the lancet 309 is in this position not operational. Put another way, the lancet 309 at this position is shielded by the hollow cylindrical part 203, which constitutes part of the housing.

From the position shown in FIG. 3, the shaft 204 is caused to rotate in a clockwise direction by action of the drive wheel 201 and drive belt 202. The drive dog 320 is engaged with the drive notch 307 in the hole 306 of the test disc member 308, and so allows rotation of the shaft 204 to result in rotation of the test disc member 308. Rotation brings the lancet 309 in front of the aperture 105. As such, a skin-covered part of a user (hereafter the part will be referred to as a user's digit, for the sake of convenience) is lanced by the lancet 309. This produces a puncture in the skin of the digit, through which blood can escape The shaft 204 is caused to rotate only by a predetermined amount, the maximum extent of travel of the lancet 309 is controlled. The penetration of the lancet 309 in the user's digit depends on a number of factors, as will be appreciated by the person skilled in the art. The amount of rotation, and thus the depth of penetration, may be definable by a user.

Subsequently, the shaft 204 is controlled to rotate in an anticlockwise direction. This causes the lancet 309 to be removed from the user's digit, and for the disc edge 305 at the cutaway portion 302 to rub the user's digit as the test disc member 208 rotates. As the test disc member 208 rotates, pressure is applied periodically to the user's digit by the ridges 322. The pressure on the user's digit increases as the first ridge "height" increases, provided that the user continues to press their digit against the aperture 105 with sufficient force. This gradual increase in pressure encourages blood to exit the puncture wound in the user's skin. At least some of this blood is absorbed into the capillary opening 324 on the crest of the first ridge 322 and is drawn through the capillary 326.

The capillary opening 324 may alternatively be located just after the crest of the ridge 322 i.e. offset clockwise of the ridge crest. This positioning may improve the efficiency of blood collection. Alternatively two or more capillary openings 324 may be provided at several locations at or near the crest of the ridge 322.

After the test disc member 208 has rotated past the crest of the first ridge, pressure on the user's digit reduces. For a period when the test disc member 208 is located between the crests of successive ridges 322, no pressure is exerted on the digit of the user. Pressure is then exerted again as the second ridge "height" increases. Blood is then absorbed via the capillary opening 324 on the second ridge.

During this part of the rotation, blood is drawn by the capillary action of the capillaries 326 to the blood collection part 315. The blood and the enzyme present in the blood collection part 315 then react.

This periodic application of pressure by successive ridges efficiently encourages blood to exit the wound. The periodicity of the pressure is determined by the spacing between successive ridges and by the speed of rotation of the test disc member 208. The frequency of the pressure applied by the ridges 322 may be consistent with the common thickness and elasticity of skin. The frequency may be such as to encourage venous blood to exit the wound. Alternatively, the frequency of the pressure may encourage plasma blood to exit the wound. The device 100 may allow the speed of rotation to be changed such that the user can control the frequency of the pressure applied by the ridges 322. For example, the device may have settings for "venous blood" and "plasma blood" and the user may select one of these settings via user inputs 101 to 103. An advantage of being able to encourage a different type of blood to exit the wound is that certain types of blood may be more suitable for testing a specific property of blood, for example the blood glucose level, haemoglobin concentration or ketone concentration.

After the blood collection stage of the rotation, the test disc member 208 is caused to continue to rotate in an anticlockwise direction. At a point in this rotation of the test disc member 208, the lowermost part of the second guide member 206 ceases to coincide with the cutaway portion 302 and so is able to exert a reaction force on the upper surface 303 of the test disc member 208. A short time thereafter, the lowermost part of the first guide member 205 becomes coincident with the cutaway portion 302, and ceases to contact the upper surface 303 of the test disc member 208. At this point, it is the second guide member 206 that prevents the first test disc member 208 moving upwards within the cartridge 206.

The shaft 204 is then caused to be rotated further in an anticlockwise direction until the notch 301 is aligned with the second guide member 206. Because at this location the first guide member 205 is coincident with the cutaway portion 302 of the test disc member 208, neither of the first or second guide members 205, 206 prevents upwards movement of the first test disc member 208. At this rotational position, the first guide member and the ridges 322 may be arranged such that there is no overlap between the test disc member 208 in the cutaway portion 302 and the first guide member 205. Alternatively, the guide members 205, 206 may prevent upward movement of the test disc member until the first guide member 205 is coincident with the first trough of the ridges 322 i.e. the area between the first and second ridges 322. At this point, the first to third disc members 208 to 210 are moved upwards by virtue of the bias means (not shown).

When the first test disc member 208 moves upwards, the drive dog 320 ceases to cooperate with the drive notch 307 of the hole 306 of the first test disc member 208. A lower surface of the drive dog 320 therefore contacts the upper surface 303 of the second test disc member 209. This prevents further upward movement of the second test disc member 209, and thus prevents further movement of the test disc member 210. At this position, the shaft 204 is caused to be rotated by the drive wheel 201 and the drive belt 202 such that the drive dog 320 is coincident with the drive notch 307 of the second test disc member 209. At this location, the second disc member 209 is able to move upwards on the shaft 204, thereby engaging the drive dog 320 with the drive notch 307 of the second test disc member 209. After the second test disc member 209 has moved upward by a distance equal to the height of the spacer member 308, further upwards movement of the second test disc member 209 is prevented by contact between the first guide member 205 and the upper surface 303 of the second test disc member 209. At this point the second guide member 206 is located within the notch 301 of the first test disc member 208. This prevents further rotation of the first test disc member 208 within the cartridge 106.

By virtue of movement up the cartridge 106 of the first to third test disc members 208 to 210, the third guide member 207 ceases to be within the notch 301 of the second test disc member 209. At this stage, the third guide member 207 does not prevent rotational movement of the second disc member 209.

At the end of the operation described above, the second test disc member 209 is in exactly the same position as was the first test disc member 208 at the position shown in FIG. 3. Furthermore, the shaft 204, and thus the drive dog 320, has the same orientation. As such, the second test disc member 209 is able to be used to elicit a blood sample from a user and test the glucose level thereof in the same way as was the first test disc member 208.

By providing a stack of test disc members 208 to 210 within the cartridge 106 and by providing a suitable physical arrangement, a cartridge 106 can be used for multiple tests. When the cartridge 106 is new, the test disc members 208 to 210 are located in the bottom half of the cartridge 106, with the uppermost test disc member being aligned with the aperture 105. As test disc members are used, the stack of test disc members moves upwards in the cartridge. When the last test disc member is used, the cartridge can be said to be spent. At this stage, all of the test disc members are located in the uppermost portion of the cartridge 106.

It will be appreciated that the number of test disc members 208 to 210 that can be accommodated within the cartridge 106, and thus the number of tests that can be provided by a cartridge 106, is a factor of the height of the cartridge 106, and the separation between corresponding parts (e.g. the upper surfaces) of adjacent test disc members 208 to 210. A taller cartridge and/or a reduced separation of test disc members increases the number of tests that can be performed using a single cartridge 106.

The lancet 309 shown in FIGS. 4 and 5 is a substantially straight rod, sharpened to a point. However, in some embodiments, the lancet 309 may instead be curved. A first end of this curved lancet may be embedded within the material of the test disc member 208, and a second end may be provided with a sharp point and extends outwardly. The curved lancet may protrudes from the disc edge 305 at the same position 312 as the straight lancet 309. The curved lancet may extend at an angle between 30 and 60 degrees from a radius line of the test disc member 208 at the position 312 where the end of the curved lancet is embedded in the test disc member. The second end of the curved lancet may be located at or just outside a circumference 311 of the test disc member 208.

At the part of the curved lancet that is adjacent the disc edge 305, the longitudinal axis of the curved lancet is at an angle X with respect to a straight line drawn between the junction between the curved lancet and the disc edge 305 and the centre of the shaft 204. The curve of the curved lancet is such that the longitudinal axis of the curved lancet at the end distant from the disc edge 305 is at an angle greater than the angle X with respect to the line drawn between the junction between the curved lancet and the disc edge 305 and the centre of the shaft 204 (the axis is different at different points on a curve). The effect is that the curved lancet is more aligned with the circumference of the test disc member 208 at its distal end than it is at the end that adjoins the disc edge 305. This has the positive effect that when the lancet penetrates a user's digit, or other body part, due to rotation of the test disc member 208, the path taken by the lancet as it penetrates the user's digit more closely matches the shape and orientation of the lancet than is experienced in a corresponding arrangement with a straight lancet.

This effect is enhanced with the curved lancet since the cylindrical form of the lancet is terminated at the distal end by an oblique cut. In particular, the distal end of the curved lancet resembles a cylinder that has been cut at an angle that is not perpendicular to the longitudinal axis of the cylinder. As such, the end face of the curved lancet has the shape of an ellipse. The ellipse has a semi-major axis and a semi-minor axis and the point that is at the end of the semi-major axis that is furthest from the disc edge 305 forms a point. The cut is made through the lancet such that the point is formed extending in a direction that is circumferential with respect to the test disc member 208. In particular, at least 1 mm of the end portion of the curved lancet is coincident with a line that is concentric with respect to the shaft.

In other embodiments, a lancet is provided that extends substantially radially from the disc edge. Operation of the device 100 comprising a radial lancet will now be described with reference to FIGS. 6 and 7. Here, the arrangement and operation is as described above with reference to FIGS. 2 to 5 unless otherwise stated. Reference numerals are retained from earlier described figures for like elements.

Figure 6:
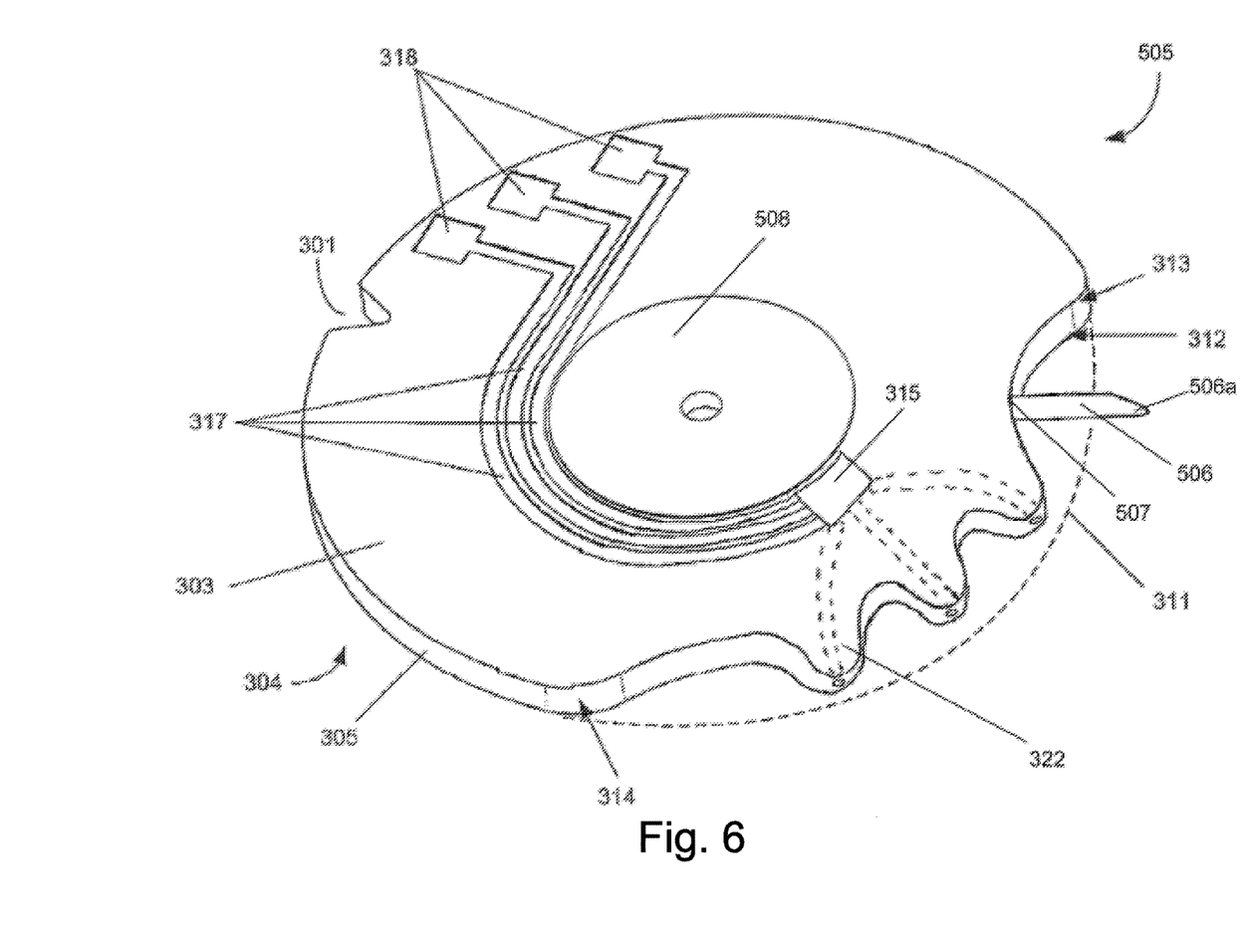
FIG. 6 illustrates a test disc member forming part of a second embodiment of the BGM of FIG. 1 in a perspective view.

Referring to FIG. 6, a test disc member 505 comprising a radial lancet is shown. A lancet 506 is provided extending from the disc edge 305 in the cutaway portion 302. In particular, the lancet 506 extends in a radial direction with respect to the centre of the test disc member 505. The lancet 506 extends from a fourth position 507, which is near to the second position 313. The fourth position 507 is further from the second position 313 than is the corresponding first position 312 in the arrangement described above with reference to FIGS. 2 to 5. However, because the lancet 506 is radial with respect to test disc member 505, a distal end 506A of the lancet 506, i.e. the end that is furthest from the centre of the test disc member 505, is at approximately the same position as the corresponding end of the lancet 309.

The majority of the test disc member 505 is substantially rigid. However, an annular centre portion 508 is comprised of an elastically deformable material. In particular, the annular centre position 508 is deformable in the presence of an externally applied force. This means that the test disc member 505 can be displaced relative to the shaft 204, as will be described in more detail below. The material used to form the annular centre portion 508 may take any suitable form, and for instance may be a rubberised plastic. The arrangement of the ridges 322, capillaries 326 and blood collection part 315 may be the same as in previous embodiments.

Figure 7:
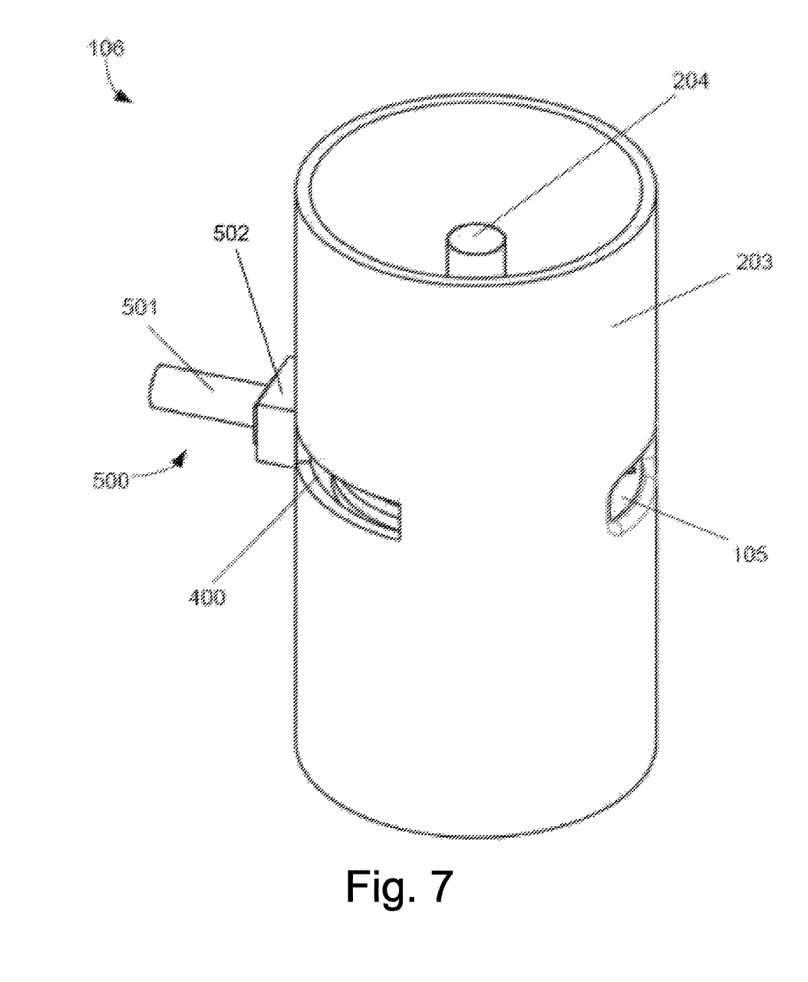
FIG. 7 illustrates components of the second embodiment of the BGM of FIG. 1 in a perspective view.

Referring now to FIG. 7, cartridge 106, adapted to operate with test disc members 505, is shown. The hollow cylindrical housing part 203 is provided with the aperture 105 and a slit aperture 400. The shaft 204 is supported centrally within the hollow cylindrical housing part 203 of the cartridge 106. However, the diameter of the shaft is less than in FIGS. 2 to 5.

A plunger arrangement 500 comprising a plunging arm 501 and a plunging head 502 is provided adjacent a plunging aperture (not shown) in the hollow cylindrical housing part 203. The plunging aperture (not shown) is located next to the slit aperture 400. The plunging aperture (not shown) is located directly opposite to the aperture 105. The plunger aperture and the slit aperture 400 may be combined to form a single aperture. The plunger aperture is configured to allow the plunging head 502 to be forced by the plunging arm 501 to a position internal to the hollow cylindrical housing part 203.

In operation, the test disc member 505 is rotated to a position at which the lancet 506 is coincident with the aperture 105. The plunging head 502 is then aligned with the test disc member 505 such that movement of the plunger arrangement 500 along the longitudinal axis of the plunging arm 501 causes the plunging head to contact the test disc member 505 and apply force to it. Since the longitudinal axis of the plunging arm 501 is radial with respect to the shaft 204, the force applied by the plunger arrangement is directed towards the shaft 204.

When the plunging head 502 has contacted the test disc member 505 on the opposite side of the test disc member to the lancet 506, the annular centre portion 508 becomes compressed on the side closest to the plunger arrangement 500 such as to allow the whole of the test disc member 505 to be displaced in the direction of the force supplied by the plunger arrangement 500. The test disc member 505 remains horizontal by virtue of the spacer members 308.

Displacement of the test disc member 505 in the direction of the force supplied by the plunger arrangement 500 results in displacement of the lancet 506 in a radial direction away from the shaft 204. In this position, the lancet 506 penetrates the skin of the user's digit. Removal of the force by the plunger arrangement 500 allows the annular centre portion 508 to return to its original form, through elastic reformation. After the plunger arrangement 500 has been fully retracted, the test disc member 505 is in its original position and the lancet 506 is retracted from the user's digit. It will be appreciated that it is the elasticity of the annular centre portion 508 of the test disc member 505 that allows the test disc member 505 to return to this position once the force applied through the plunger arrangement 500 is removed.

After removal of the force supplied by the plunger arrangement 500, the test disc member 505 can be rotated by the drive wheel 201 and the drive belt 202 so as to provide milking of the user's digit and collection of blood by the ridges 322 and capillary openings 324. After a measurement of blood glucose level is taken (described in more detail below), the test disc member 505 is rotated further anti-clockwise so that the second guide member 206 is aligned with the notch 301, and thus the test disc member 505 is allowed to move upwards within the cartridge 106. As a result, the test disc member that is immediately below the first test disc member 505 also moves upwards within the cartridge 106 and is provided to be coincident with the aperture 105, the slit aperture 400 and the plunger aperture (not shown). Subsequent application of a plunging force by the plunger arrangement 500 causes a lancet 506 of the second test disc member to be forced out of the aperture 105. The process can be repeated for other test disc members included in the cartridge 106.

An advantage of the arrangement shown in FIGS. 6 to 7 is that a rotational arrangement can be used whilst allowing the lancet 506 to penetrate a user's skin in a longitudinal direction with respect to the lancet 506. Another advantage is that puncture can occur at any desired location, for instance on the end of the user's digit, instead of puncturing occurring slightly on the side of the end of the digit.

Another advantage is that the arrangement can allow the penetration depth of the lancet 506 to be easily predictable.

Furthermore, it allows the penetration or puncturing depth to be adjustable. In particular, the adjustment of the penetration depth can be achieved by a mechanical arrangement that limits movement of the plunger arrangement towards the shaft 204. Alternatively, it can be achieved in an electro-mechanical manner by measuring the location or displacement of some part of the mechanism and ceasing applying an energising voltage to a solenoid or other transducer that is used to affect movement of the plunger arrangement 500. The penetration depth may be specified by a user. The depth may be specified by a user may be achieved through software or firmware control of rotation of the shaft 204. The penetration depth may be defined by the user for example using one or more of the first, second and third inputs 101 to 103. For instance, the first and second inputs 101, 102 may be increase and decrease respectively, with the third input 103 being a select or confirm input. The value defining the depth may be stored in memory. Penetration depth control is important to many users since lancet penetration usually is painful and since penetration depth control allows users some control over their experience.

Figure 8:
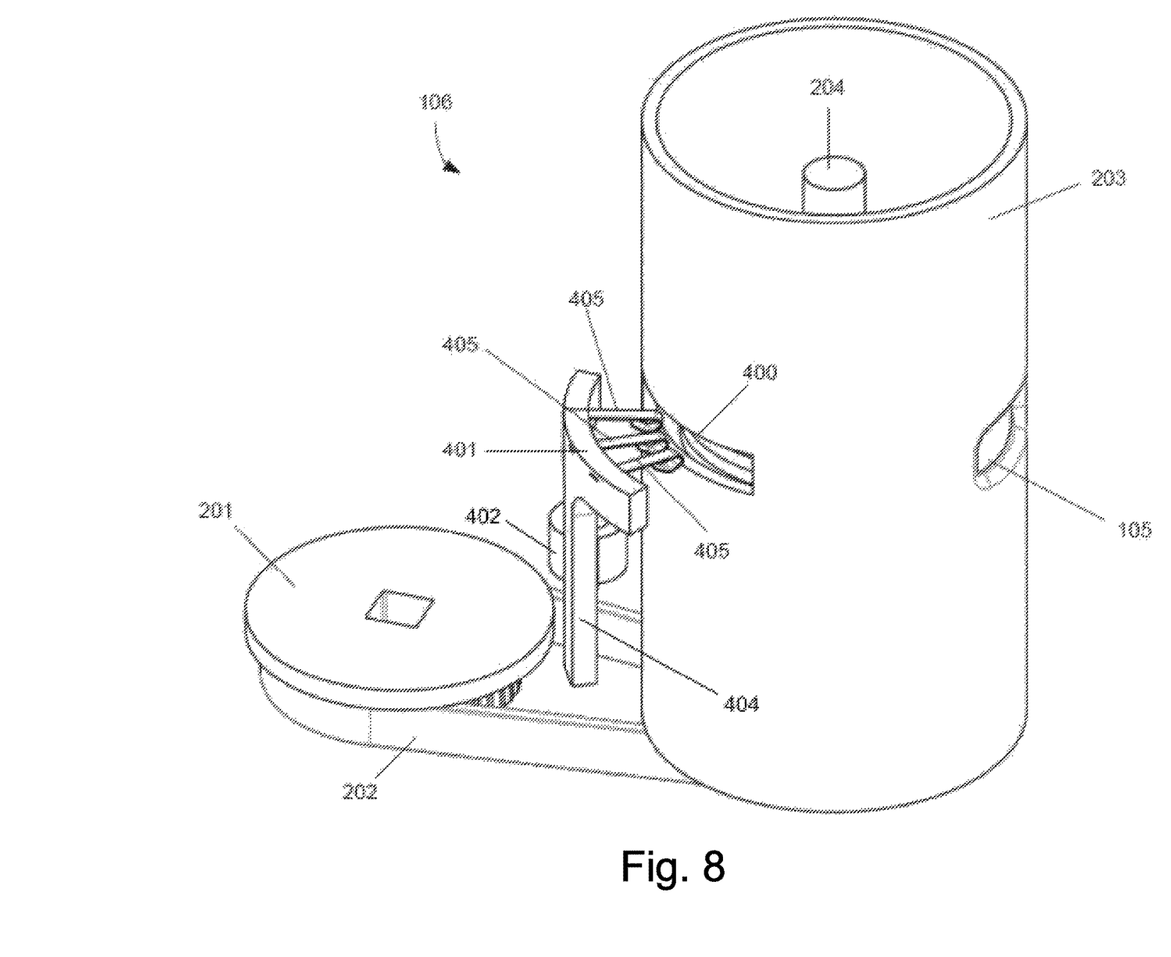
FIG. 8 is a perspective view of components of the BGM of FIG. 1.

Reference will now be made to FIG. 8, which illustrates a mechanism for connection of the contact pads 318 of the test disc members 208, 505 to measurement circuitry (not shown).

In FIG. 8 the hollow cylindrical housing part 203 is shown with the aperture 105 and the shaft 204 located as described above. A slit aperture 400 is provided in the hollow cylindrical housing part 203. The slit aperture 400 is located at substantially the same height as the aperture 105. However, the slit aperture 400 is located on a side of the hollow cylindrical housing part 203 that is substantially opposite the aperture 105.

The slit aperture 400 does not coincide with the elongate aperture 110 that is formed at the front side of the BGM 100. As such, the slit aperture 400 is not visible when the cartridge 106 is in place within the BGM 100.

Adjacent to the slit aperture 400 is located a swing arm 401. The swing arm 401 is rotatable about a spindle 402. The spindle 402 has an axis that is parallel to the axis of the shaft 204. The axis of the spindle 402 is located above the drive belt 202. A connecting arm (not visible) connects the spindle 402 to the swing arm 401. In this example, the connecting arm is connected to the swing arm 401 by a vertical connector 404. The vertical connector 404 allows the spindle 402 on which the connecting arm is mounted to be located at a different vertical position to the swing arm 401. The spindle 402, the connecting arm and the vertical connector 404 are arranged such that when the connecting arm is rotated on the axis of the spindle 402 the swing arm 401 is moved towards the shaft. The movement of the swing arm 401 is substantially radial with respect to the shaft 204.

Mounted on the swing arm 401 are first to third electrical contact terminals 405. Each includes a generally horizontal arm and a depending contact head. The electrical contact terminals 405 are made of a resilient conductive material, for instance metal. The depending contact heads are angled at their ends furthest from the swing arm 401.

In one position, shown in FIG. 8, the electrical contact terminals 405 are supported by the swing arm 401 such that the dependent contact heads are located within the slit aperture 400 or alternatively outside of the hollow cylindrical housing part 203. After the test disc member 208, 505 has been rotated such that the ridges 322 have moved past the aperture 105, the shaft 204 is configured to stop the rotation of the test discs 208, 505 such that the contact pads 318 are coincident/aligned with the slit aperture 400. As the test disc member 208, 505 is held in this position, the connecting arm is caused to rotate around the axis of the spindle 402 such that the swing arm 401 moves towards the shaft 204. The arrangement is such that the depending contact heads of the electrical contact terminals 405, but not the horizontal arms, come into contact with the contact pads 318 as the electrical contact terminals 405 move into the volume above the upper surface 303 of the test disc member 208, 505. The resilient properties of the electrical contact terminals 405 causes the electrical contact terminals to be forced against the contact pads 318. As such, an electrical connection is provided between the horizontal arms of the electrical contact terminals 405 and the blood collection part 315. Electronic measuring means (not shown) connected to the electrical contact terminals 405 operate to pass a voltage through the contact terminals 405 and the blood collection part 315 and to take measurements of electrical parameters, from which a measurement of an analyte concentration level, for example a blood glucose level, can be determined.

The connecting arm is controlled to remain in this position for a predetermined time or alternatively until it is detected that a blood glucose level measurement has been made, after which the connecting arm is caused to rotate around the shaft 402 so as to remove the electrical contact terminals 405 from the position above the upper surface of the test disc member 208, 505. Once the electrical contact terminals 405 have been retracted, the test disc member 208, 505 is rotated anticlockwise so as to allow the test disc members 208, 505 to move upwards on the shaft 204.

It will be appreciated that the maximum permissible height dimension of the electrical contact terminals 405 is determined by the height of the spacer member 308. A thicker spacer member allows larger electrical contact terminals 405 to be used. However, this is at the expense of an increase in separation between adjacent test disc members 208, 505, and thus a reduced capacity for the cartridge 106. The use of electrical contact terminals 405 including a horizontal arm and a depending contact head allows the height dimension of the electrical contact terminals to be minimised whilst allowing good electrical contact between the electrical contact terminals and the contact pads 318 and also allowing the electrical contact terminals 405 to operate correctly over a sufficient number of cycles.

Figure 9:
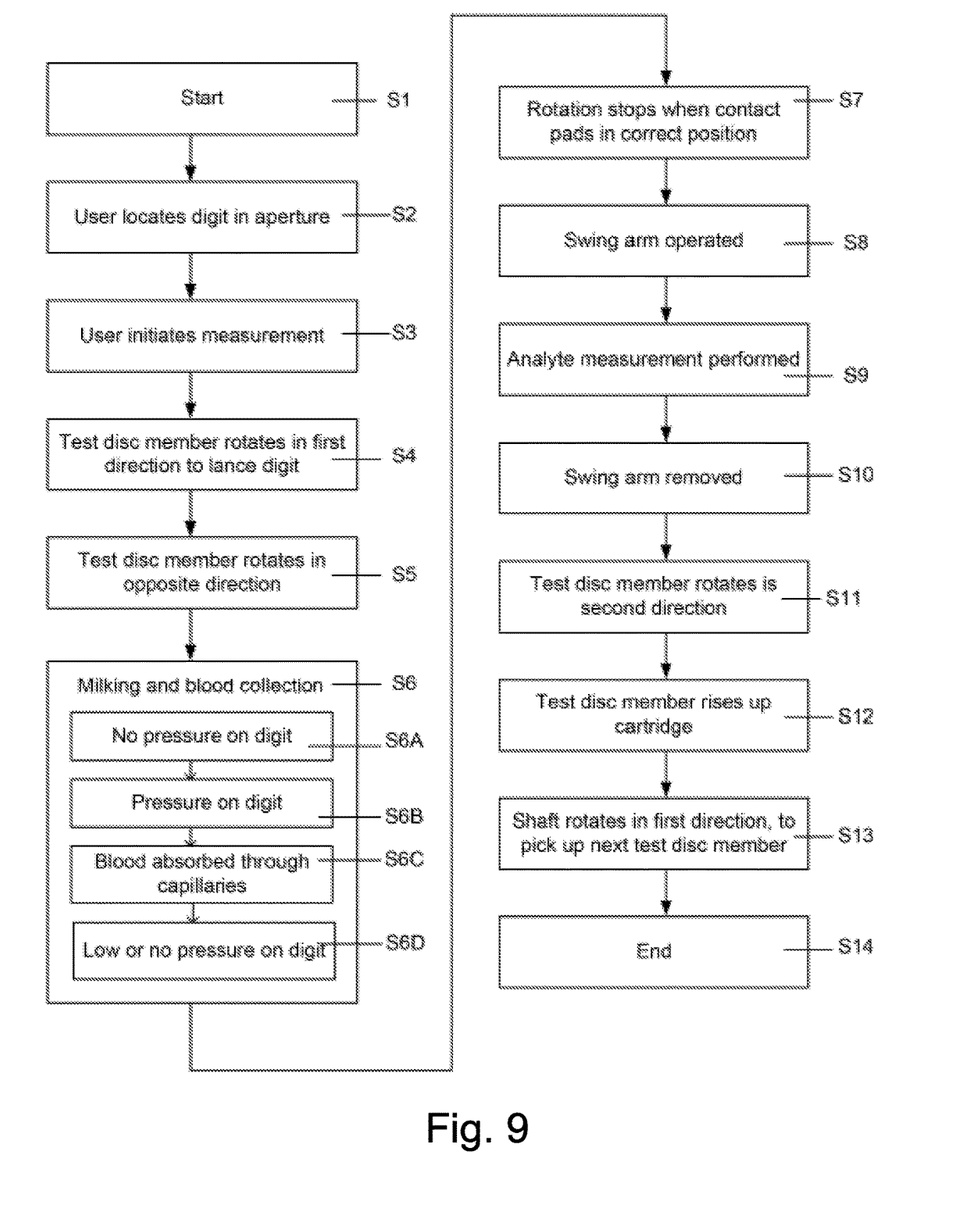
FIG. 9 is a flowchart illustrating operation of the first embodiment of the BGM of FIG. 1.

Operation of the blood glucose meter 100 will now be described with reference to the flowchart of FIG. 9. Operation starts at step S1. At step S2, the user locates their digit in the aperture 105. As mentioned above, the user forces their digit into the aperture 105 with a pressure or force that is suitable to allow lancing and blood collection. At step S3, the user initiates blood glucose measurement. This involves the user pressing one of the inputs 101 to 103. This is detected by the microprocessor 212 by way of the keys interface 215. The software/firmware stored in the ROM 214 uses the key input to call a function or to execute a software module. The software/firmware stored in the ROM 214 then causes the microprocessor 212 to issue a command to a motor attached to the drive wheel 201 through the motor interface 217 to rotate the shaft 204 in a clockwise direction. The software/firmware controls the extent of the rotation. At step S4, the amount of rotation is sufficient to lance the user's digit with the lancet 309. The software/firmware stored in the ROM 214 then causes the microprocessor 212 to control the motor to rotate the shaft 204 in the opposite direction, at step S5.

As the test disc member rotates anticlockwise, milking and blood collection occurs at step S6. Firstly, at step S6A, there is no pressure applied by the test disc member on the digit. This step relates to the period before the first ridge 322 has contacted the user's digit. At step S6B, pressure is exerted by the first ridge 322 on the user's digit. This step relates to the period in which the "height" of the ridge 322 is increasing. At step S6C, blood is absorbed into the capillaries 326 through the capillary openings 324 provided on the ridges 322. This step may coincide with the time when the pressure on the user's digit is highest. At step S6D, there is low or no pressure on the user's digit. This step relates to the period in between ridges 322. Thus, steps S6B to S6D may be repeated several times according to the number of ridges 322 present. In some embodiments, the ridges 322 may be sized such that a part of the user's digit is in contact with one or more of the ridges 322 at all times during this part of the rotation. In this case, the pressure may become "low", but not disappear entirely.

It will be appreciated that in the embodiments described using the test disc member 208, the user's digit or other body part is lanced from the side in a clockwise direction by rotational action of the lancet 309. In the subsequent rotation, the ridges 322 apply pressure to the user's digit in an anticlockwise direction i.e. on the other side of the user's digit from the puncture wound. This directional application of pressure by the ridges 322 results in an efficient expression of blood from the wound. Furthermore, the wound is not contacted by the ridges 322 while pressure is applied. This reduces the amount of pain experienced by the user while allowing a blood droplet to form on the surface of the user's digit. This blood droplet can then be absorbed by the capillaries 326 as the wound location passes the capillary openings 324.

At step S7, the software/firmware causes the microprocessor 212 to control the motor to cease rotation when the shaft 214 is such that the contact pads 318 are coincident with the slit aperture 400. At step S8, the software/firmware controls a motor such as to cause the swing arm 401 to be rotated towards the shaft 204. The software/firmware stored in the ROM 214 is such that the microprocessor 212 causes only the required amount of travel of the swing arm 401. At this point, the analyte interface circuit 219 is coupled directly to the blood collection part 315, which has been provided with blood from the user's digit. At step S9, analyte measurement is performed. This involves the analyte interface circuit 219 providing voltages to the electrical connection contacts 318, and thus to the blood collection part 315, and measuring parameters of resulting signals. The measured parameters, particularly voltage parameters, are used by the software/firmware stored in the ROM 214, as executed by the processor 212, to calculate a blood glucose measurement level of the user. The blood glucose measurement is then caused by the software/firmware to be displayed on the display 104 through action of the microprocessor 212 on the display drive 216. At step S10, the swing arm is caused to be removed by action of the microprocessor 212, under control of the software stored in the ROM 214, the motor interface 217 and the motor (not shown).

At step S11, the software/firmware results in the microprocessor 212 controlling the drive disc 201 to rotate anticlockwise. Rotation continues until the notch 301 on the test disc member is coincident with the guide 206. At step S12, the test disc member rises up the cartridge 106. In the case where biasing of the test discs up the cartridge 106 is provided by a bias means, for instance a spring, step S12 requires no action on part of the software/firmware and microprocessor 212, although there may be a pause before the next step. In embodiments where movement of the test disc members along the shaft 204 occurs through driving action, step S12 involves the microprocessor 212, under control of the software/firmware stored in the ROM 214, controlling a motor through the motor interface 217. Subsequently, at step S13, the microprocessor 212, under control of the software/firmware stored in the ROM 214, causes the shaft 204 to rotate again in a clockwise direction and to cease rotating when the drive dog 320 engages with the drive slot 307 of the next test disc member in the cartridge 106. At this stage, the test disc members rise up the cartridge 106 slightly.

The operation ends at step S14.

Various modifications and alternative features can be used in connection with the above-described embodiments. Some alternatives now follow.

Although in the above the shaft 204 is said to be driven by a drive wheel 201 that is coupled to the shaft 204 by a drive belt 202, the drive may instead be direct (i.e. the drive mechanism is coupled directly to the shaft 204), or connection may be made by a notched belt, a vee belt, or by a direct gear mechanism. Instead of an electric motor, a clockwork drive could be used. A clockwork drive mechanism has a number of advantages, particularly where access to batteries or battery chargers or electricity supplies are limited. In the embodiments in which a clockwork mechanism is used, the user can be sure that the BGM 100 will not cease operating because of drained batteries. A clockwork mechanism may be particularly suited to developing countries and emerging markets.

In embodiments in which an electrical motor is used to drive the shaft 204, preferably control is exerted over the motor by software. In this way, the speed of rotation can easily be controlled. Additionally, the extent of rotation can more easily be controlled. The motor may be a stepper motor.

Alternatively, a mechanical drive arrangement may be present, for instance using a lever or other device for manual actuation. A suitable mechanism may be one similar to those previously used in SLR cameras.

The swing arm 401 may be actuated in any suitable way. For instance, it may be driven by the same motor or mechanism as the shaft 204. Alternatively, it may be driven by a separate motor. In either case, the rotation of the swing arm 404 may be affected by a cam mechanism, or by a pin and slot (track path) mechanism. In the event of an electric motor being used, the motor preferably is software driven. The motor preferably is a stepper motor.

The mechanical arrangement may include a mechanism by which a bias means, for instance a mechanical compression spring, is biased and then released in order to push the electrical contact terminals 405 into place. The terminals 405 can then be retracted by the swing arm 401 using a rotating motion. The overall mechanism can be termed a latch type trigger mechanism.

Instead of a swing arm 401 being used to rotate the electrical contact terminals 405 into place, the contact pads 318 may instead be located on the disc edge 305, allowing the use of fixed electrical contact terminals 405. The electrical contact terminals may include a brush or other deformable feature such that the test disc members 208 to 210, 505 can move whilst in contact with the electrical contact terminals without damage occurring to any of the components. Similar arrangements are used in brushed DC motors. In this case the electrical contact terminals 405 could be flexible finger contacts that rest on the periphery of the test disc members 208 to 210, 505 in order to contact the contact pads 318.

Alternatively, instead of a swing arm 401, a mechanism may be used to affect longitudinal movement of the electrical contact terminals 405 into place to contact the contact pads 318.

The conductive tracks 317 and the contact pads 318 may be formed by leadframe. Alternatively, overmoulding may be used. Alternatively, printed circuit board (PCB) printing may be used.

Optionally, each of the test disc members 209, 210, 505 is separated from adjacent test disc members by a membrane (not shown in the drawings). In this case, the membrane preferably fits closely to the internal surface of the hollow cylindrical housing part 203. An effect of the membrane is to reduce the possibility of disc cross-contamination. Use of a membrane may allow the test disc members 208 to 210, 505 to have a reduced separation than would be the case without the use of a membrane.

In the above, the test disc members 505 are said to be biased upwards by a bias means, for instance a compression spring. Alternative mechanisms for moving the test disc members 505 up the cartridge may be used. For instance, a threaded lifting cam may be provided on the shaft 204 or alternatively on the interior surface of the hollow cylindrical housing part 203. Alternatively, the test disc members 505 may remain stationary, with the aperture 105 and the drive dog 320 instead being moved along the axis of the cartridge 106. Movement of the aperture 105 may be achieved by the use of a sliding door in an elongated slot. Movement of the door allows a different strip to be revealed at the aperture 105.

Additionally, the test disc members 505 may include a disinfecting or cleaning portion that contacts the digit before lancing. This can reduce risk of infection of the wound and also can increase accuracy in particular by removing any glucose from the skin (as may occur after eating fruit etc.).

Although the test disc members 208 are illustrated as lancing in a clockwise direction, and applying pressure via the ridges 322 in an anticlockwise direction, the direction of lancing and milking may be reversed.

The invention claimed is:

1. An apparatus for eliciting a blood sample, the apparatus comprising:
   a test disc member releasably mounted on a rotatable shaft, the test disc member having an outer edge, the outer edge including a first portion having a generally circular outer circumference and a second cutaway portion, wherein the cutaway portion comprises a plurality of ridges configured to collect blood from a user;
   an aperture; and
   a lancet attached to the test disc member and protruding from the cutaway portion of the outer edge of the test disc member, the lancet and the test disc member being configured such that the lancet pierces skin of the user's body part that is adjacent to the aperture as the test disc member is rotated in a first direction;

wherein the test disc member is configured to collect blood from the user via the plurality of ridges when rotated in a second direction that is opposite the first direction after the skin of the user's body part is pierced; and wherein the apparatus is configured to rotate the test disc member via rotation of the shaft in the first direction to cause the lancet to pierce the skin of the user's body part that is adjacent to the aperture and configured to rotate the test disc member via rotation of the shaft in the second direction to collect blood from the user via the plurality of ridges.

2. The apparatus according to claim 1, further comprising a housing, wherein the aperture is formed in a wall of the housing, and wherein the shaft is mounted inside the housing.

3. The apparatus according to claim 1, wherein the plurality of ridges comprises three ridges.

4. The apparatus according to claim 1, wherein each ridge of the plurality of ridges has a partly or completely curved profile.

5. The apparatus according to claim 1, wherein a first end of a capillary is disposed on a ridge of the plurality of ridges.

6. The apparatus according to claim 5, wherein the first end of the capillary is disposed approximately at a crest of the ridge of the plurality of ridges.

7. The apparatus according to claim 5, further comprising a blood collection part supported on or within the test disc member, wherein the capillary extends through a body of the test disc member and terminates at the blood collection part.

8. The apparatus according to claim 7, wherein the blood collection part comprises an absorbent material that contains an enzyme for blood glucose determination.

9. The apparatus according to claim 7, wherein the blood collection part has a higher capillary pull force than a capillary pull force of the capillaries.

10. The apparatus according to claim 1, wherein the apparatus is configured to control the speed of rotation of the test disc member by controlling the rotation of the rotatable shaft such that the spacing between adjacent ridges of the plurality of ridges in combination with the control in the speed of the rotation of the test disc member enables control of a frequency of a periodic pressure applied to skin of the user's body part.

11. The apparatus according to claim 10, wherein the apparatus is configured for a speed of rotation of the test disc member and a spacing between adjacent ridges resulting in a frequency of a periodic pressure applied to skin of the user's body part that encourages venous blood to exit a puncture wound in the user's body part or alternatively wherein the apparatus is configured for a speed of rotation of the test disc member and a spacing between adjacent ridges resulting in a frequency of a periodic pressure applied to skin of the user's body part that encourages plasma blood to exit a puncture wound in the user's body part.

12. The apparatus according to claim 1 wherein, prior to the rotation in the first direction, a distal end of the lancet is not co-located with the aperture.

13. The apparatus according to claim 1, wherein the test disc member further comprises at least two electrical contact points connected to a blood collection part for communication with a meter for determining a parameter of blood chemistry.

14. A method for eliciting a blood sample, the method comprising:

providing a test disc member releasably mounted on a rotatable shaft, the test disc member having an outer edge, the outer edge including a first portion having a generally circular outer circumference and a second cutaway portion, wherein the cutaway portion comprises a plurality of ridges;

providing an aperture;

providing a lancet protruding from the cutaway portion of the outer edge of the test disc member;

rotating the test disc member in a first direction so that the lancet pierces skin of a user's body part that is adjacent to the aperture; and subsequent to rotating the test disc member in the first direction, rotating the test disc member in a second direction that is opposite the first direction, thereby collecting blood from the user via the plurality of ridges.

* * * * *